US012773244B2

(12) United States Patent
Koay et al.

(10) Patent No.: US 12,773,244 B2
(45) Date of Patent: Oct. 27, 2026

(54) PROXIMAL FEMUR HOOK PLATE

(71) Applicant: DePuy Synthes Products, Inc., Raynham, MA (US)

(72) Inventors: Kenny Koay, West Chester, PA (US); Jessica Galie, West Chester, PA (US); Troy Probst, Wilmington, DE (US); Peter Fatone, Exton, PA (US); Bryan Fritz, Coatesville, PA (US); Mike Brace, Lansdale, PA (US); Glenna Smith, West Chester, PA (US); George J. Haidukewych, Orlando, FL (US); Karl Stoffel, Bottmingen (CH); Cory A. Collinge, Fort Worth, TX (US); Frank A. Liporace, Fort Worth, TX (US); Bruce H. Ziran, Atlanta, GA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 17/750,468

(22) Filed: May 23, 2022

(65) Prior Publication Data

US 2022/0280209 A1 Sep. 8, 2022

Related U.S. Application Data

(62) Division of application No. 15/918,680, filed on Mar. 12, 2018, now Pat. No. 11,344,344.

(Continued)

(51) Int. Cl.
*A61B 17/80* (2006.01)
*A61B 17/74* (2006.01)

(52) U.S. Cl.
CPC ............ *A61B 17/742* (2013.01); *A61B 17/74* (2013.01); *A61B 17/80* (2013.01);
(Continued)

(58) Field of Classification Search
CPC ....... A61B 17/742; A61B 17/74; A61B 17/80; A61B 17/8004; A61B 17/809; A61B 17/8061; A61B 17/82
See application file for complete search history.

(56) References Cited

U.S. PATENT DOCUMENTS 4,565,193 A 1/1986 Streli
4,973,332 A 11/1990 Kummer
(Continued)

FOREIGN PATENT DOCUMENTS

CN 102497830 A 6/2012
FR 3010300 A1 3/2015
(Continued)

OTHER PUBLICATIONS

U.S. Appl. No. 15/918,680, filed Mar. 12, 2018.

*Primary Examiner* — Tracy L Kamikawa
(74) *Attorney, Agent, or Firm* — Condo Roccia Koptiw LLP

(57) ABSTRACT

A bone plate for treating periprosthetic fractures includes a head portion to be positioned along a greater trochanter of a bone. The head portion includes pairs of bone fixation element receiving openings extending therethrough from a first surface of the plate which, when the plate is in an operative position, faces away from the bone, and a second surface which, when the plate is in the operative position, faces toward the bone. A pair of cable holes extend through the head portion from a first longitudinal side connecting the first and second surfaces to a second longitudinal side connecting the first and second surfaces. The head portion includes a pair of hooks for engaging a superior ridge of the greater trochanter. The plate also includes a shaft portion extending distally from the head portion to extend along a portion of the bone distal of the greater trochanter.

20 Claims, 3 Drawing Sheets

Related U.S. Application Data

(60) Provisional application No. 62/470,766, filed on Mar. 13, 2017, provisional application No. 62/470,753, filed on Mar. 13, 2017.

(52) U.S. Cl.
CPC ...... *A61B 17/8004* (2013.01); *A61B 17/8057* (2013.01); *A61B 17/8061* (2013.01)

(56) References Cited

U.S. PATENT DOCUMENTS

| | | | | |
|---|---|---|---|---|
| 5,190,545 | A | 3/1993 | Corsi et al. | |
| 6,066,141 | A | 5/2000 | Dall et al. | |
| 6,338,734 | B1 | 1/2002 | Burke et al. | |
| 7,207,993 | B1 | 4/2007 | Baldwin et al. | |
| 7,229,444 | B2 | 6/2007 | Boyd | |
| 7,255,701 | B2 | 8/2007 | Allen et al. | |
| 7,335,204 | B2 | 2/2008 | Tornier | |
| 7,951,176 | B2 | 5/2011 | Grady et al. | |
| 8,062,296 | B2 | 11/2011 | Orbay et al. | |
| 8,142,434 | B2 | 3/2012 | Bluechel | |
| 8,197,521 | B2 | 6/2012 | Sixto, Jr. et al. | |
| 8,267,972 | B1 | 9/2012 | Gehlert | |
| 8,328,809 | B2 * | 12/2012 | Wenk | A61B 17/80 606/70 |
| 8,394,130 | B2 | 3/2013 | Orbay et al. | |
| 8,728,080 | B2 | 5/2014 | Boomer et al. | |
| 8,728,082 | B2 | 5/2014 | Fritzinger et al. | |
| 8,764,809 | B2 * | 7/2014 | Lorenz | A61B 17/74 606/283 |
| 8,795,342 | B2 | 8/2014 | Reisberg | |
| 8,808,333 | B2 | 8/2014 | Kuster et al. | |
| 8,834,532 | B2 | 9/2014 | Velikov et al. | |
| 8,894,693 | B2 * | 11/2014 | Petit | A61B 17/809 606/280 |
| 9,138,267 | B2 * | 9/2015 | Cavallazzi | A61B 17/74 |
| 9,283,010 | B2 | 3/2016 | Medoff et al. | |
| 10,231,762 | B2 | 3/2019 | Steinhauer et al. | |
| 2005/0070904 | A1 * | 3/2005 | Gerlach | A61B 17/8061 606/291 |
| 2006/0217722 | A1 | 9/2006 | Dutoit et al. | |
| 2006/0235401 | A1 * | 10/2006 | Baldwin | A61B 17/842 606/291 |
| 2007/0270849 | A1 | 11/2007 | Orbay et al. | |
| 2009/0105717 | A1 | 4/2009 | Bluechel | |
| 2009/0312758 | A1 | 12/2009 | Petit et al. | |
| 2010/0234896 | A1 | 9/2010 | Lorenz et al. | |
| 2010/0262194 | A1 * | 10/2010 | Wagner | A61B 17/80 606/286 |
| 2010/0292698 | A1 | 11/2010 | Hulliger et al. | |
| 2011/0071573 | A1 * | 3/2011 | Sixto | A61B 50/36 606/286 |
| 2011/0224671 | A1 | 9/2011 | Koay et al. | |
| 2012/0123484 | A1 | 5/2012 | Lietz et al. | |
| 2013/0211461 | A1 * | 8/2013 | Christen | A61B 17/8061 606/286 |
| 2014/0243837 | A1 | 8/2014 | Mebarak | |
| 2014/0243906 | A1 | 8/2014 | Cavallazzi et al. | |
| 2015/0127011 | A1 | 5/2015 | Dunlop et al. | |
| 2015/0157373 | A1 | 6/2015 | Wolf et al. | |
| 2015/0257802 | A1 | 9/2015 | Wolf et al. | |
| 2016/0166298 | A1 | 6/2016 | Mighell et al. | |
| 2016/0192968 | A1 * | 7/2016 | Chan | A61B 17/1728 470/10 |
| 2017/0252080 | A1 | 9/2017 | Steinhauer et al. | |

FOREIGN PATENT DOCUMENTS

| | | | |
|---|---|---|---|
| JP | 2005-537087 | A | 12/2005 |
| JP | 2007-506452 | A | 3/2007 |
| JP | 2007-289698 | A | 11/2007 |
| JP | 2008-532709 | A | 8/2008 |
| JP | 2010-500134 | A | 1/2010 |
| JP | 2011-502641 | A | 1/2011 |
| JP | 3177020 | U | 7/2012 |
| JP | 2016-540576 | A | 12/2016 |
| WO | 2007/103333 | A2 | 9/2007 |
| WO | 2011/003494 | A1 | 1/2011 |
| WO | 2015/088760 | | 6/2015 |

* cited by examiner

PROXIMAL FEMUR HOOK PLATE

PRIORITY CLAIM

This present application is a divisional of U.S. Ser. No. 15/918,680 filed Mar. 12, 2018, now U.S. Pat. No. 11,344, 344, which claims priority to U.S. Provisional Patent Application Ser. Nos. 62/470,766 and 62/470,753 both filed on Mar. 13, 2017, the disclosure of both is expressly incorporated herein by reference.

BACKGROUND

Proximal femur fractures are often treated with a bone plate positioned on an outer surface of the femur extending across a fracture site. In some cases, however, particularly for periprosthetic fractures, fixation of the bone plate may be difficult where, for example, an implant such as a THA (Total Hip Arthroplasty) has previously been implanted. In these cases, bone fixation elements to fix the plate to the bone must be inserted through the bone without interfering with a stem of the THA or other intramedullary device.

SUMMARY

The present embodiments are directed to a bone plate for treating periprosthetic fractures comprises a head portion sized and shaped to be positioned along a greater trochanter of a bone, the head portion including a plurality of pairs of bone fixation element receiving openings extending therethrough from a first surface of the bone plate which, when the bone plate is in an operative position, faces away from the bone, and a second surface which, when the bone plate is in the operative position, faces toward the bone, and a pair of cable holes extending through the head portion from a first longitudinal side connecting the first and second surfaces to a second longitudinal side connecting the first and second surfaces, a proximal end of the head portion including a pair of hooks for engaging a superior ridge of the greater trochanter and a shaft portion extending distally from the head portion to extend along a portion of the bone distal of the greater trochanter.

BRIEF DESCRIPTION

DETAILED DESCRIPTION

Figure 1:
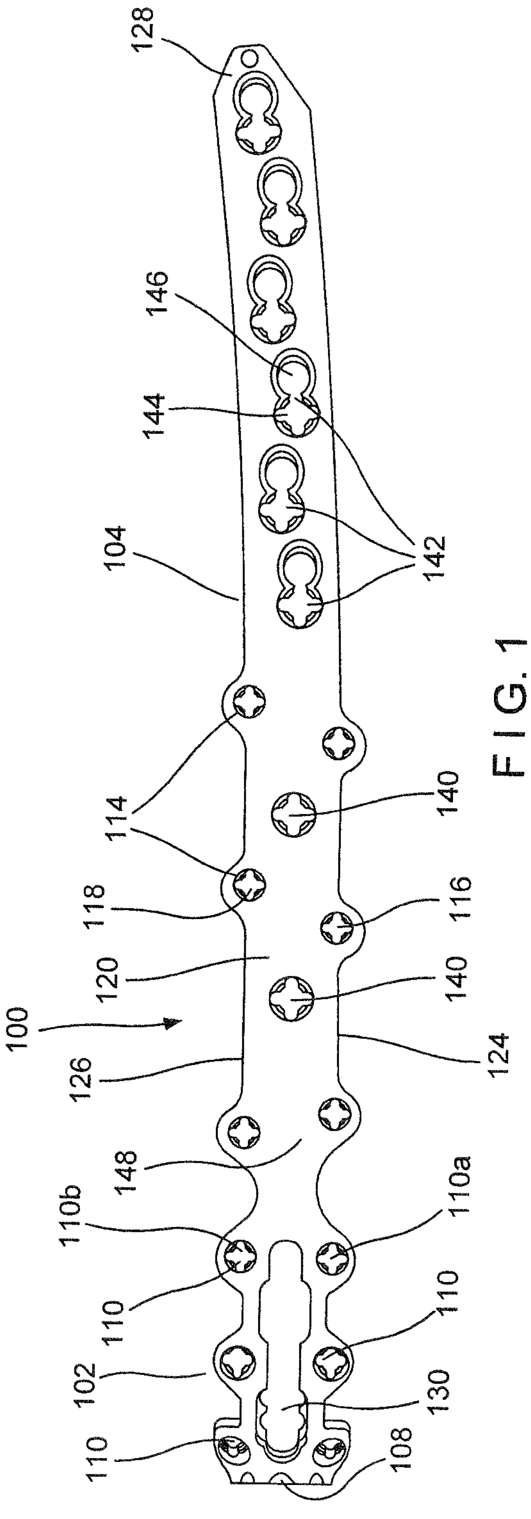
FIG. 1 shows a top plan view of a bone plate according to an exemplary embodiment of the present disclosure.
Figure 2:
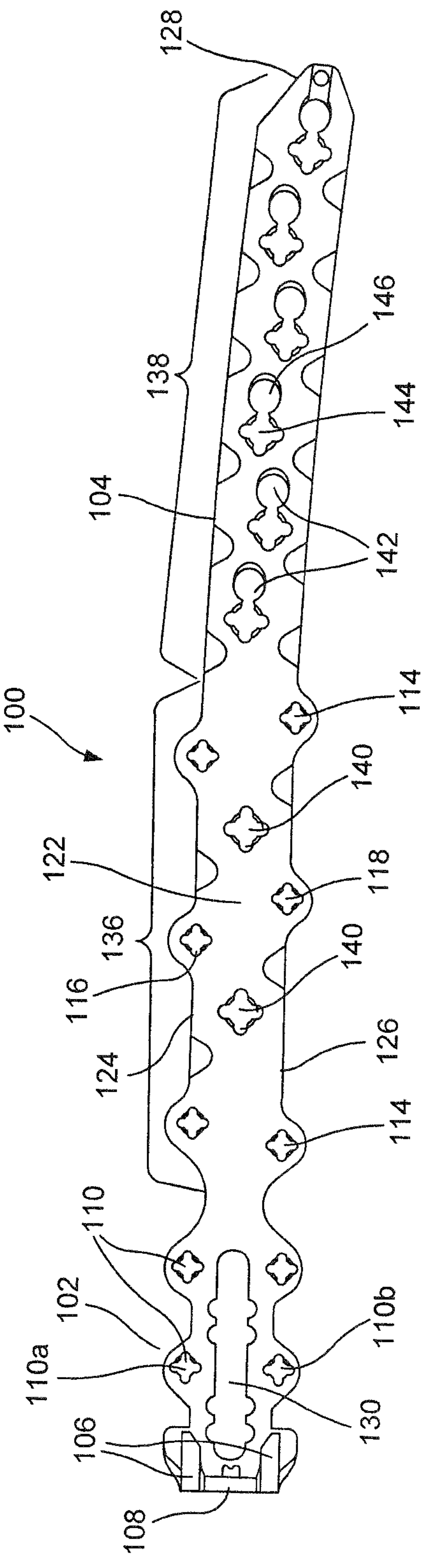
FIG. 2 shows a bottom plan view of the bone plate of FIG. 1.
Figure 3:
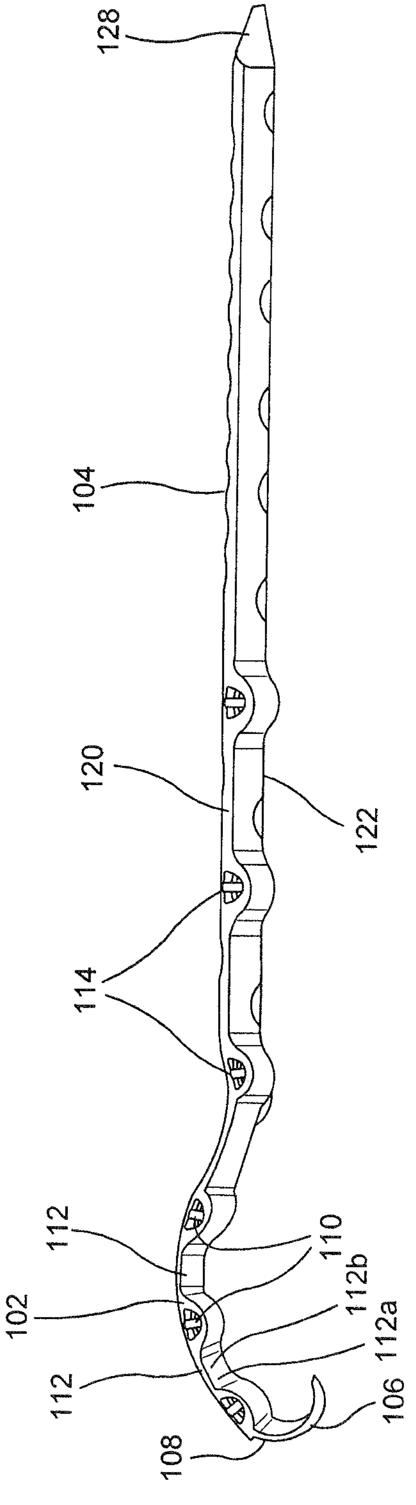
FIG. 3 shows a longitudinal side view of the bone plate of FIG. 1.
Figure 4:
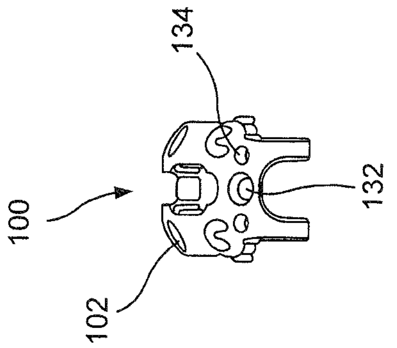
FIG. 4 shows a side view of the bone plate of FIG. 1, from a proximal end of the plate.

The present invention may be understood with respect to the following description and the appended drawings, wherein like elements are referred to with the same reference numerals. The present invention relates to the treatment of fractures and, in particular, relates to the treatment of periprosthetic proximal femur fractures. Exemplary embodiments describe a bone plate comprising a head portion configured to be positioned over a portion of a greater trochanter of a femur and a shaft portion extending distally therefrom to be positioned over a portion of a shaft of the femur. The head portion may include a pair of hooks extending from a proximal end thereof to engage a superior ridge of the greater trochanter. The head portion may also include both cable holes for providing cable compression of the greater trochanter and bone fixation element holes for preventing greater trochanteric escape. The shaft portion includes a plurality of pairs of holes on opposite sides of the shaft portion and axially offset from one another. That is, a first one of the holes of each pair is positioned on a first side of a longitudinal axis of the plate while the second one of the holes of the pair is positioned on a second side of the longitudinal axis, so that, bone fixation elements may be placed on both an anterior side and a posterior side of the prosthetic (e.g., THA stem). It will be understood by those of skill in the art that the terms “proximal” and “distal” are intended to refer to a direction relative to a bone (e.g., femur) on which the bone plate is to be positioned with proximal indicating a direction toward the hip while distal indicates a direction toward the knee.

Figure 7:
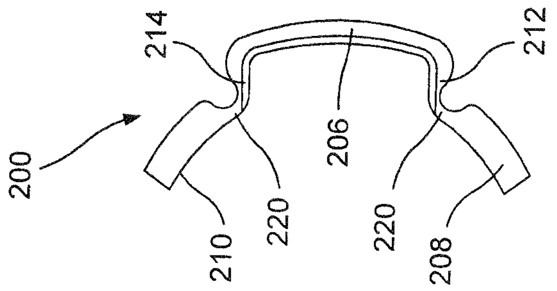
FIG. 7 shows a side view of the attachment plate of FIG. 5.
Figure 6:
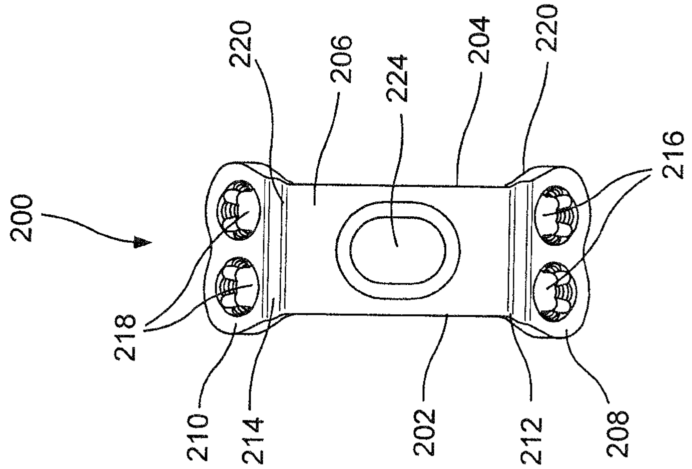
FIG. 6 shows a top plan view of the attachment plate of FIG. 5.
Figure 5:
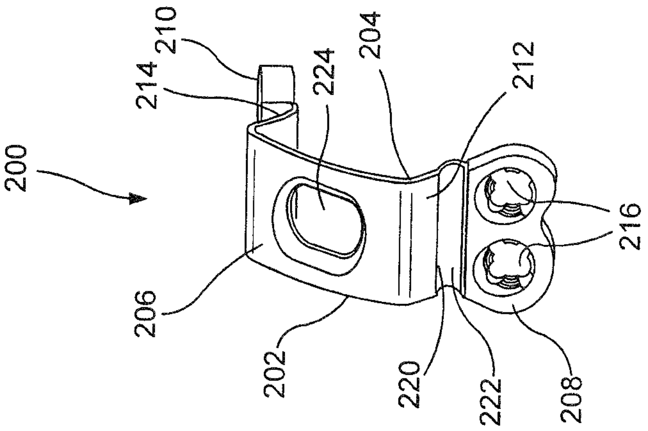
FIG. 5 shows a perspective view of an attachment place mountable over a portion of the bone plate of FIG. 1.

FIGS. 1-7 show a system according to an exemplary embodiment of the present disclosure for treating periprosthetic fractures such as, for example, Vancouver Type A fractures (i.e., fractures in the greater trochanter) and/or Vancouver Type B fractures (i.e., fracture in the proximity of a stem of a previously placed THA prosthetic or other intramedullary device). The system according to a first embodiment comprises a bone plate 100, as shown in FIGS. 1-4, configured to be implanted along a proximal portion of the femur, the bone plate 100 including a head portion 102 configured to be positioned along a greater trochanter of a femur and a shaft portion 104 extending distally therefrom to be positioned along a length of the proximal femur extending distally from the greater trochanter. The head portion 102 of this embodiment includes a pair of hooks 106 at a proximal end 108 thereof for engaging a superior ridge of the greater trochanter along with both bone fixation element receiving openings 110 and cable holes 112 so that the head portion 102 may be fixed to the greater trochanter via both bone fixation elements inserted through the bone fixation element receiving openings 110 and via a cable circled about a proximal end of the bone and fixed to the head portion 102 via the cable holes 112. The shaft portion 104 includes a plurality of pairs of offset holes 114. Each pair of holes includes a first hole 116 on a first side of the longitudinal axis and a corresponding second hole 118 on a second side of the longitudinal axis opposite the first side so that bone fixation elements may be inserted through first and second holes 116, 118 to provide fixation on both an anterior side of the prosthetic and a posterior side of the prosthetic. The first and second holes 116, 118 of each pair are offset or staggered relative to one another along a length of the shaft portion 104 to reduce the risk that stress risers will be generated in the bone due to the insertion of two bone fixation elements at the same axial position along the bone. A locking attachment plate 200, as shown in FIGS. 5-7, may be mounted over the shaft portion 104 of the proximal femur plate 100, between axially adjacent pairs of offset holes 114, to provide additional fixation openings, if so desired. Those skilled in the art will understand that the head portion of any of the described bone plates may be formed as a separate element that is either independently mountable on the bone itself (i.e., just the head portion without a distally extending shaft) or which is mountable on a separate bone plate formed as a shaft extending distally along the femur.

As shown in FIGS. 1-4, and as described above, the bone plate 100 includes the head portion 102 configured to be positioned over the greater trochanter and the shaft portion 104 extending distally therefrom to be positioned along a proximal length of the femur distal of the greater trochanter. The bone plate 100 extends along a longitudinal axis from the proximal end 108 to a distal end 128 and is defined via a first surface 120 which, when the bone plate 100 is in an operative position along a bone, faces away from the bone, and a second surface 122 which, when the bone plate 100 in the operative position, faces the bone. Longitudinal sides 124, 126 extend longitudinally between the first and second surfaces 120, 122, from the proximal end 108 to the distal end 128.

The head portion 102 extends along a curve corresponding to a shape of the greater trochanter. The proximal end 108 includes the pair of hooks 106 configured to engage the superior ridge at a proximal end of the greater trochanter. Each of the hooks 106 extends from the proximal end 108 distally along a curve selected to match a shape of the underlying portion of the greater trochanter. As would be understood by those skilled in the art, the two hooks 106 may differ from one another in length and/or radii of curvature to accommodate asymmetries in the structure of the portion of the greater trochanter underlying each hook. The hooks 106 are positioned to prevent interference with a prosthetic (e.g., THA stem) previously inserted into the bone. In particular, a first one of the hooks 106 is positioned so that, when the plate 100 is in a desired position on the bone, a first one of the hooks 106 extends anterior relative to the prosthetic while the other of the hooks 106 extends posterior relative to the prosthetic. In use, the hooks 106 may be hammered and/or otherwise driven into the superior ridge of the greater trochanter to facilitate engagement of the hooks 106 with the greater trochanter.

The bone fixation element openings 110 extend through the head portion 102 from the first surface 120 to the second surface 122 and are oriented along the head portion 102 in pairs. In particular, each pair of bone fixation element receiving openings 110 includes a first opening 110*a* extending through the head portion 102 on a first side of the longitudinal axis of the bone plate and a second opening 110*b* extending through the head portion 102 on a second side of the longitudinal axis opposite the first side so that bone fixation elements inserted through the first and second openings 110*a*, 110*b* may extend anterior and posterior of an implanted intramedullary prosthetic. The first and second openings 110*a*, 110*b* may be aligned along a length of the bone plate 100. In particular, the configurations of the bone fixation element receiving openings 110 permit bone fixation elements to be inserted antero-inferior and postero-inferior of the prosthetic towards a calcar of the bone.

Each of the bone fixation element openings 110 of this embodiment extends laterally beyond portions of the head portion 102 along which openings 110 do not extend. In other words, the bone fixation element openings 110 project laterally beyond portions of the longitudinal sides 124, 126 between the openings to reduce the width of the plate 100 in these areas (e.g., distance between longitudinal sides 124, 126) as compared to customary trauma plates and to facilitate the insertion of bone fixation elements around the prosthetic. In one embodiment, central axes along which the bone fixation element receiving openings 110 extend through the head portion 102 may be aligned with the longitudinal sides 124, 126. In the exemplary embodiment shown, the head portion 102 includes three pairs of bone fixation element receiving openings extending therethrough. A longitudinal spacing between adjacent bone fixation element receiving openings is, in this embodiment, uniform along a length of the head portion 102. The bone fixation element receiving openings 110 may be configured as variable angle holes through which bone fixation elements such as, for example, variable angle locking screws, may be inserted at an angle relative to central axes thereof. It will be understood by those of skill in the art, however, that this configuration of bone fixation element receiving openings 110 is exemplary only and that the head portion 102 may have any number of bone fixation element receiving openings extending therethrough in any of a variety of spacings and configurations so long as bone fixation elements are insertable therethrough on an anterior and posterior side of a prosthetic.

The head portion 102 may also include pairs of cable holes 112 extending therethrough, from the first longitudinal side 124 to the second longitudinal side 126. Each pair of cable holes extends through the head portion 102 between adjacent pairs of bone fixation element receiving openings 110 so that placement of cables do not interfere with a placement of bone fixation elements through the openings 110. As will be understood by those of skill in the art, a cable may be circled about a proximal end of the femur (e.g., about a lesser trochanter of the femur), with portions of the cable passing through first and second ones 112*a*, 112*b* of the pair of cable holes 112. The cable may be tensioned to provide compression of the greater trochanter. The head portion 102 may further include an elongated opening 130 elongated along the longitudinal axis and extending through from the first surface 120 to the second surface 122 so that the elongated opening 120 is in communication with the first and second holes 112*a*, 112*b* of each of the pairs of cable holes 112. A crimp may be received within the elongated opening to be crimped over portions of the cable inserted through first and second cable holes 112*a*, 112*b* and passing across the elongated opening 130 to maintain the cable in the tensioned configuration. The crimp may reside within the elongated opening 130 so that no portion of the crimp protrudes substantially beyond the first surface 120. In an exemplary embodiment, the proximal portion includes two pairs of cable holes 112. Fixation of the head portion to the greater trochanter via both cable(s) and bone fixation elements provide compression while minimizing the changes of the greater trochanter slipping from the bone plate 100.

The proximal end 108 of the head portion of this embodiment includes a proximal opening 132 along with suture openings 134 extending therethrough from the first surface 120 to the second surface 122. This proximal opening 132 is configured to receive a portion of an insertion device for aiding in implantation of the bone plate 100. Alternatively, a bone fixation element such as, for example, a variable angle locking screw may be inserted therein to provide additional fixation. The suture openings 134 similarly extend through the head portion 102 from the first surface 120 to the second surface 122 so that a suture may be passed therethrough to suture surrounding tissue thereto.

The shaft portion 104 extends distally from the head portion 102 to be positioned along a proximal portion of the femur distal of the greater trochanter. The shaft portion 104 may extend along a curve along and about the longitudinal axis to correspond to a shape of the femur. The shaft portion 104 may include a proximal portion 136 configured to be positioned along a portion of the femur including the prosthetic extending therethrough and a distal portion 138 extending distally from the proximal portion 136 and configured to extend along a portion of the femur distal of the prosthetic.

The plurality of pairs of offset holes 114 extend through the proximal portion 136 of the shaft portion 104. Each pair of offset holes 114 includes the first hole 116 extending through the shaft portion 104 from the first surface 120 to the second surface 122 on the first side of the longitudinal axis and the second hole 118 extending through the shaft portion 104 from the first surface 120 to the second surface 122 on the second side of the longitudinal axis. The first and second holes 116, 118 extend along opposing sides of the shaft portion 104 so that bone fixation elements inserted through first and second holes 116, 118 will extend anterior and posterior to the prosthetic inserted in the bone. The first and second holes 116, 118 are also offset or staggered (5-15 mm and preferably 7.9 mm, or angled at 16.4° to 41.4° relative to the longitudinal axis of the plate 100) relative to one another along a length of the proximal portion 136 to minimize stress risers. For each first hole 116, the corresponding second hole 118 (the second hole 118 closest to this first hole 118 along the longitudinal axis) is offset from the its paired first hole 116 along the longitudinal axis of the plate 100. In one embodiment, a first pair of offset holes 114 proximate a proximal end 148 of the shaft portion 104 is configured to target the lesser trochanter when the plate 100 is positioned over the femur as desired, as described above.

In one embodiment, the second hole 118 (e.g., one of the holes 116, 118 on a posterior side of the prosthetic in the operative position) may be positioned distally of the first hole 116 since it has been found that a posterior aspect of the femur has better bone quality. Thus, it may be desired to have holes along the posterior aspect lower (i.e., more distal) so that bone fixation elements may be inserted through better quality bone, lower on the bone where a cross-sectional area of the prosthetic (e.g., stem) is smaller, maximizing a fixation of the bone plate 100 to the bone. This configuration of first and second holes 116, 118, however, is not required. In another embodiment, one or more of the pairs of offset holes 114 may have the second hole 118 distal of the corresponding first hole 116 while the first hole 116 may be distal of the second hole 118 for the remaining pair(s) of offset holes 114. For example, in the embodiment shown, the pair of offset holes 114 immediately proximate the proximal end 148 of the shaft portion 104 has the first hole 116 distal of the second hole 118 while the remaining pairs of offset holes 114 include the second holes 118 distal of the first holes 116. It will be understood by those of skill in the art that the pairs of offset holes 114 may have any of a variety of configurations so long as the first and second holes 116, 118 are offset relative to one another.

Similarly to the bone fixation element receiving openings 110 of the head portion 102, the first and second holes 116, 118 of the pair of openings 114 extend laterally beyond the portions of the first and second longitudinal sides 124, 126 between the holes 116, 118 to minimize the width of the plate 100. Similarly to the bone fixation element receiving openings 110, in one embodiment, central axes of the first and second holes 116, 118 may be aligned with longitudinal sides 124, 126. The first and second holes 116, 118 may, in one embodiment, be configured as variable angle holes configured to receive bone fixation elements such as, for example, variable angle locking screws, therein at angles relative to the central axes. The first and second holes 116, 118, along with bone fixation element receiving openings 110 may, for example, be configured as 3.5 mm variable angle holes. 3.5 mm screws may be particularly useful for treating periprosthetic fractures since once a prosthetic has been inserted into the bone, there is less bone through which bone fixation elements may be inserted along an anterior and posterior side of the prosthetic.

A distance between adjacent pairs of offset holes 114 in this embodiment is selected to accommodate the attachment plate 200 in the space between adjacent pairs of the offset holes 114, as shown in FIGS. 5-7. That is, the spacing is selected to allow the attachment plate 200 to be mounted over the reduced width portion of the plate 100 between adjacent pairs of offset holes 114 without interfering with any of the first and second holes 116, 118. In other words, a distal one of the first and second holes 116, 118 of a first pair of offset holes 114 should be separated from a proximal one of the first and second holes 116, 118 of a second, adjacent pair of offset holes 114 by a distance of at least a length (along the longitudinal axis of the plate 100) of the locking attachment plate 200.

The proximal portion 136 of this embodiment also includes attachment openings 140 extending through a portion thereof between adjacent pairs of offset holes 114 for attaching the attachment plate 200 to the proximal femur plate 100, as will be described in greater detail below. Screws or other fixation elements are inserted into a portion of the attachment plate 200 and through the attachment openings 140 to fix the attachment plate 200 to the plate 100. The attachment openings 140 may be configured as variable angle holes or any other hole capable of receiving a fixation element therein. In one embodiment, the attachment openings 140 may be configured as 5.0 mm variable angle holes which may receive fixation elements such as variable angle locking screws and/or positioning pins through which portions of a cable may extend. In one exemplary embodiment, the proximal portion 136 of the shaft portion 104 may include three (3) pairs of offset holes 106 and two (2) attachment openings 140. It will be understood by those of skill in the art, however, that the number of pairs of offset holes 106 may vary depending on a desired length of the proximal portion 108 (e.g., length of the stem prosthetic) and a length of the locking attachment plate 200. For cases in which the locking attachment opening 134 is not used for coupling the locking attachment plate 200 to the proximal femur plate, a fixation element such as, for example, a variable angle positioning pin may be inserted therein to couple the shaft portion 104 to the bone with a cable.

The distal portion 138 of the shaft portion 104, in the operative position, may extend along a portion of the femur distal of a distal end of the stem prosthetic. The distal portion 138 may include a plurality of fixation openings 142 along a length thereof. In one embodiment, one or more of the fixation openings 142 may be offset with respect to the longitudinal axis of the shaft portion 104. In other words, central axes along which the fixation openings 142 extend through the distal portion 138 may extend parallel to the longitudinal axis, on either side thereof. The fixation openings 142, however, do not extend beyond either of the first and second longitudinal edges 1324. 126 since bone fixation elements inserted therethrough are not required to extend to the side of a prosthetic. In one embodiment, the fixation openings 142 may be configured as combination holes including a first portion 144 configured as a variable angle opening and a second portion 146 being configured as a compression opening. Thus, various bone fixation elements such as, for example, variable angle locking screws, compression screws, and variable angle positioning pins with cables may be inserted into the fixation openings 118. Although the exemplary embodiments of the bone plate 100 are described and shown as including proximal and distal portions 136, 138, the bone plate 100 may also be manufactured as a short plate having just the proximal portion 136 with the pairs of offset holes 114 extending therethrough.

As shown in FIGS. 5-7, the locking attachment plate 200 extends from a proximal end 202 to a distal end 204 along a longitudinal axis of the attachment plate 200 and is configured to be mounted over the shaft portion 104 of the proximal femur plate 100, between adjacent pairs of offset holes 114. The locking attachment plate 200 includes a body portion 206, sized and shaped to be mounted over the proximal portion 136 of the shaft portion 104 of the bone plate 100, along with a first laterally extending wing 208 and/or a second laterally extending wing 210 extending therefrom. Each of the first and second laterally extending wings 208, 210 includes bone fixation element receiving openings 212, 214 extending therethrough. As will be described in greater detail below, the locking attachment plate 200 may be useful for cases in which additional fixation of the bone plate 100 is desired and/or where the bone plate 100 must accommodate larger portions of the stem or other prosthetic.

The body portion 206 is sized and shaped to be mounted or seated over first surface 120 of the shaft portion 104 of the bone plate 100 which, in the operative position, faces away from the bone. In particular, the body portion 210 may have a substantially bracket-like shape which, in the operative position, extends along the surface of the bone plate 100 and over the longitudinal sides 124, 126. The body portion 206 may further include a body opening 224 extending therethrough. A connecting screw or other fixation element maybe inserted through the body opening 224 and one of the attachment openings 140 of the bone plate 100 to couple the locking attachment plate 200 to the bone plate 100 in a desired position therealong. As described above, a length of the body portion 206 (i.e., a distance between the proximal and distal ends 202, 204 thereof) corresponds to a distance between adjacent pairs of offset holes 114.

First and second laterally extending wings 208, 210 extend from first and second longitudinal sides 212, 214 of the body portion 206, respectively. Thus, in the operative position, the first and second laterally extending wings 208, 210 extend laterally beyond the longitudinal sides 124, 126 of the bone plate 100 to contact the bone. Each of the first and second laterally extending wings 208, 210 includes bone fixation element receiving openings 216, 218, extending therethrough. In one embodiment, each of the first and second wings 208, 210 includes two bone fixation element receiving openings 216, 218. Preferably, two bone fixation elements may be inserted through the openings 216, 218 at a diagonal relative to one another—a first fixation element through one of the openings 216 extending through the first wing 208 and a second fixation element through one of the openings 218 extending through the second wing 210 such that the bone fixation elements are staggered along a length of the bone. Similarly to the offset holes 114 of the bone plate 100, this may be done to prevent stress risers. In one embodiment, the bone fixation element receiving openings 216, 218 may be configured as variable angle holes.

Connecting portions 220 of the locking attachment plate 200 connecting the body portion 206 with the first and/or second wings 208 may include grooves 222 extending therealong so that, the first and second wings 208, 210 may be bent relative to the body portion 206 to adjust the attachment plate 200 to a specific patient's bone. As noted above, the first and second wings 208, 210 should come into contact with the bone when the bone plate 100 and locking attachment plate 200 assembly is positioned along the bone.

Since the first and second wings 208, 210 extend beyond the longitudinal sides 124, 126 of the bone plate 100, the attachment plate 200 may be particularly useful for situations in which the bone plate 100 must be fixed to a portion of bone having a large portion of the prosthetic extending therethrough. In other words, a distance between the openings 216, 218 is greater than a distance between the first and second holes 116, 118 of the pair of offset holes 114 to accommodate a larger portion of the stem. Alternatively or, in addition, the attachment plate 200 may be used to provide fixation in addition to the fixation provided by the pairs of offset holes 114.

According to an exemplary surgical method using the above-described system, the bone plate 100 may be positioned along the proximal femur to treat a periprosthetic fracture by pounding the pair of hooks 106 into the superior ridge of the greater trochanter and positioning a remaining portion of the head portion 102 along the greater trochanter and the shaft portion 104 along a portion of a shaft of the proximal femur extending distally from the greater trochanter. In particular, the proximal portion 136 of the shaft portion 104 may be positioned along a portion of the bone in which the prosthetic may be received. The distal portion 138 may be positioned along a portion of the bone distal of the prosthetic. The first pair of offset holes 114 proximate the proximal end 148 may be substantially aligned with the lesser trochanter. Once the bone plate 100 has been positioned along the bone, in a desired position as described above, bone fixation elements such as, for example, screws, and other fixation element such as, for example, cables, may be used to fix the bone plate 100 to the bone.

In particular, bone fixation elements are inserted into desired ones of the bone fixation element receiving openings 110 of the head portion 102, the first and second holes 116, 118 of the pairs of offset holes 114 of the proximal portion 136 and/or the fixation holes 142 of the distal portion 138 to fix the bone plate 100 to the bone in the desired position. One or more cables may be inserted through the pairs of cable holes 112 to provide compression of greater trochanter. The cable may be circled and tensioned about the proximal end of the femur so that portions of the cable may be crimped via a crimp residing within the elongated opening 130. While the cable(s) provide compression, bone fixation elements inserted through the first and second holes 110*a*, 110*b* of the bone fixation element receiving openings provide resistance to rotational and translational forces. Other fixation elements such as, for example, positioning pins with cables may be inserted through, for example, attachment openings 140 and/or fixation openings 142 to provide additional cable fixation.

Alternatively or, in addition, where it is desired to provide holes which may accommodate a larger portion of the prosthetic and/or where it is desired to provide additional fixation, the attachment plate 200 may be mounted to the bone plate 100 between adjacent pairs of offset holes 114. The attachment plate 200 may be assembled with the bone plate 100 prior to implantation of the bone plate 100. The attachment plate 200 and the bone plate 100 may be assembled by inserting a fixation screw through the body opening 224 and a corresponding one of the attachment openings 140. Once assembled, the wings 208, 210 may be bent relative to the body portion 206, if desired, to customize the assembly to the patient's specific anatomy. Bone fixation elements are inserted through a desired one of the first openings 216 and a desired one of the second openings 218.

As described above, bone fixation elements should be inserted through the first and second openings in a diagonal configuration to prevent stress risers. Upon fixation of the plate assembly, as described, surrounding tissue may be sutured to the plate 100 via suture holes 134.

It will be understood by those of skill in the art that modifications and variations may be made in the structure and methodology of the present invention, without departing from the spirit or scope of the invention. Thus, it is intended that the present invention cover the modification and variations of this invention, provided that they come within the scope of the appended claims and their equivalents.

What is claimed is:

1. A system for treating a periprosthetic fracture, comprising:

a bone plate including a first surface which, when the bone plate is in an operative position, is configured to face away from a bone, and a second surface which, when the bone plate is in the operative position, is configured to face toward the bone, the bone plate including:

a head portion sized and shaped to be positioned along a greater trochanter of the bone, the head portion including a plurality of pairs of bone fixation element receiving openings extending therethrough from the first surface of the bone plate to the second surface of the bone plate, and a pair of cable holes extending through the head portion from a first longitudinal side of the bone plate connecting the first and second surfaces to a second longitudinal side of the bone plate connecting the first and second surfaces, a proximal end of the head portion including a pair of hooks configured to engage a superior ridge of the greater trochanter; and a shaft portion that extends in a distal direction from the head portion, a proximal portion of the shaft portion including:

i. a plurality of bone fixation holes that extend from the first surface to the second surface, all of the plurality of bone fixation holes arranged as a plurality of pairs of offset bone fixation holes, each of the pairs of the offset bone fixation holes including a first bone fixation hole at a first side of a longitudinal axis of the bone plate and a second bone fixation hole at a second side of the longitudinal axis opposite the first side, the first and second bone fixation holes of each pair offset relative to one another along a longitudinal direction defined by the longitudinal axis a first distance, wherein adjacent ones of the pairs of the offset bone fixation holes are separated from each other by respective gaps that each extend a respective distance along the longitudinal direction greater than the first distance;

wherein the bone fixation holes on one of the first or second sides of the longitudinal axis are unevenly spaced apart from each other in a longitudinal direction and the bone fixation holes on the other of the first or second sides of the longitudinal axis are evenly spaced apart from each other; and ii. at least one attachment opening, an attachment opening of the at least one attachment opening disposed in one of the respective gaps, wherein the pairs of the offset bone fixation holes are longitudinally adjacent each other, such that the attachment opening is the only opening that is disposed between adjacent ones of the pairs of the offset bone fixation holes, and the plurality of bone fixation holes arranged as the plurality of pairs of the offset bone fixation holes and the at least one attachment opening are the only holes adapted for receiving fixation elements through the proximal portion of the shaft portion; and an attachment plate including a body portion and a pair of laterally extending wings that extend from the body portion, wherein the attachment plate has a body opening that extends through the body portion and is configured to receive a plate fixation element that is sized to be received in the attachment opening so as to secure the attachment plate to the bone plate, wherein in the operative position, the laterally extending wings are configured to contact the bone, the attachment plate defining first and second bone fixation element receiving openings extending through respective ones of the laterally extending wings, the first and second bone fixation element receiving openings positioned and configured to receive respective bone screws so as to directly fix the laterally extending wings to the bone.

2. The system of claim 1, wherein the proximal portion of the shaft portion is configured to extend along a portion of a shaft of the bone in which a prosthetic extends, and bone fixation elements inserted through the first and second bone fixation holes are configured to extend anterior and posterior of the prosthetic.

3. The system of claim 2, wherein each of the pair of laterally extending wings extends laterally beyond a respective one of the first and second longitudinal sides of the bone plate, the first bone fixation element receiving opening of the attachment plate extending through a first one of the pair of laterally extending wings and the second bone fixation element receiving opening of the attachment plate extending through a second one of the pair of laterally extending wings.

4. The system of claim 3, wherein a lateral offset distance between the first and second bone fixation element receiving openings of the attachment plate is greater than a lateral offset distance between the first and second bone fixation holes of each pair of the plurality of pairs of the offset bone fixation holes.

5. The system of claim 3, wherein each of the pair of laterally extending wings of the attachment plate is bendable with respect to the body portion.

6. The system of claim 2, wherein each of the plurality of pairs of bone fixation element receiving openings of the head portion includes a first opening on the first side of the longitudinal axis and a second opening on the second side of the longitudinal axis.

7. The system of claim 2, wherein the shaft portion includes a distal portion extending in the distal direction from the proximal portion configured to extend along a portion of the bone distal of the prosthetic, in the operative position, the distal portion including a plurality of fixation openings.

8. The system of claim 7, wherein each of the plurality of fixation openings comprises a variable angle opening and a compression opening that is open to the variable angle opening.

9. The system of claim 8, wherein adjacent ones of the plurality of fixation openings are spaced from each other along the longitudinal direction a respective distance that is less than the distance of the gap.

10. The system of claim 9, wherein the adjacent ones of the plurality of fixation openings are on opposite sides of the longitudinal axis, and offset toward the longitudinal axis with respect to the plurality of bone fixation holes.

11. The system of claim 2, wherein the at least one attachment opening comprises a plurality of attachment openings each disposed in different ones of the respective gaps, and the body opening of the attachment plate is configured to receive the plate fixation element that is sized and configured to be selectively received in each of the plurality of attachment openings so as to selectively fix the attachment plate to the bone plate at multiple locations on the bone plate along the longitudinal direction.

12. The system of claim 1, wherein the head portion includes an elongated opening extending therethrough, from the first surface to the second surface, in communication with the pair of cable holes, so that a crimp for crimping a portion of a cable is receivable therein.

13. The system of claim 1, wherein the pair of hooks extend from the proximal end of the head portion along a curve pointed in the distal direction.

14. The system of claim 1, wherein the body portion has a proximal end and a distal end that are spaced from each other a distance along a direction defined by the longitudinal axis of the bone plate, and the distance corresponds to the distance of the gap between adjacent ones of the pairs of the offset bone fixation holes.

15. The system of claim 1, wherein a common plane passes through each of the body opening and the first and second bone fixation element receiving openings of the attachment plate, wherein the common plane is oriented perpendicular to the distal direction.

16. The system of claim 1, wherein the plurality of pairs of the offset bone fixation holes comprise a first pair of offset bone fixation holes and a second pair of offset bone fixation holes, a distance between the first bone fixation hole of the first pair of offset bone fixation holes and the first bone fixation hole of the second pair of offset bone fixation holes being greater than a distance between the second bone fixation hole of the first pair of offset bone fixation holes and the second bone fixation hole of the second pair of offset bone fixation holes.

17. The system of claim 16, wherein a first one of the at least one attachment opening is longitudinally between the second bone fixation hole of the first pair of offset bone fixation holes and the second bone fixation hole of the second pair of offset bone fixation holes.

18. The system of claim 17, wherein a second one of the at least one attachment opening is longitudinally between the first bone fixation hole of the second pair of offset bone fixation holes and the second bone fixation hole of a third pair of offset bone fixation holes.

19. The system of claim 1, wherein the plurality of pairs of the offset bone fixation holes comprise a first pair of offset bone fixation holes and a second pair of offset bone fixation holes, the first bone fixation hole of the first pair being spaced apart from the proximal end of the head portion by a first spacing distance, the second bone fixation hole of the first pair being spaced apart from the proximal end of the head portion by a second spacing distance, wherein the second spacing distance is greater than the first spacing distance; and the first bone fixation hole of the second pair being spaced apart from the proximal end of the head portion by a third spacing distance, the second bone fixation hole of the second pair being spaced apart from the proximal end of the head portion a fourth spacing distance, wherein the third spacing distance is greater than the fourth spacing distance, and wherein the fourth spacing distance is greater than the second spacing distance.

20. The system of claim 9, wherein the plurality of pairs of the offset bone fixation holes further comprise a third pair of offset bone fixation holes, the first bone fixation hole of the third pair being spaced apart from the proximal end of the head portion by a fifth spacing distance, the second bone fixation hole of the third pair being spaced apart from the proximal end of the head portion by a sixth spacing distance, wherein the fifth spacing distance is greater than the sixth spacing distance, and wherein the sixth spacing distance is greater than the fourth spacing distance.

* * * * *